United States Patent [19]

Teasdale

[11] Patent Number: 5,604,125
[45] Date of Patent: Feb. 18, 1997

[54] FORMULATIONS OF PLANT CULTURE MEDIA AND APPLICATIONS THEREFOR

[75] Inventor: Robert D. Teasdale, Robina, Australia

[73] Assignee: FB Investments Pty Ltd., Queensland, Australia

[21] Appl. No.: 400,451

[22] Filed: Mar. 7, 1995

Related U.S. Application Data

[63] Continuation of Ser. No. 50,353, filed as PCT/AU91/00509, Nov. 4, 1991, published as WO92/07460, May 14, 1992, abandoned.

[30] Foreign Application Priority Data

Nov. 2, 1990 [AU] Australia ................... PK3157

[51] Int. Cl.$^6$ ............... C12N 5/04; C12N 5/00
[52] U.S. Cl. ..................... 435/422; 435/431
[58] Field of Search ............ 435/240.4, 240.54, 435/240.48, 240.49

[56] References Cited

U.S. PATENT DOCUMENTS

| | | | |
|---|---|---|---|
| 4,672,035 | 6/1987 | Davidonis et al. | 435/240 |
| 4,818,693 | 4/1989 | Stuart et al. | 435/240.49 |
| 5,034,326 | 7/1991 | Puelman et al. | 435/240.4 |
| 5,036,007 | 7/1991 | Gupta et al. | 435/240.45 |

FOREIGN PATENT DOCUMENTS

| | | |
|---|---|---|
| 2568088 | 11/1987 | Australia . |
| 1584854 | 2/1981 | United Kingdom . |
| 9001058 | 2/1990 | WIPO . |
| 9105854 | 5/1991 | WIPO . |

OTHER PUBLICATIONS

Reilly et al 1976 Georgia Forest Research Paper #86 (publisher, Georgia Forest Research Council, Macon, GA) pp. 1–9.

Mohammed et al 1986 New Zealand J. Foreshy Sci 16(3):297–305.

Dougall 1980 In Plant Tissue Culture as a Source of Biochemical; CRC Press pp. 21–57. (Staba, edition).

*Primary Examiner*—Patricia R. Moody
*Attorney, Agent, or Firm*—Amster, Rothstein & Ebenstein

[57] ABSTRACT

An aqueous medium for plant tissue culture is provided including a nutritively effective concentration of reduced nitrogen, preferably in the form of an amino acid such as arginine employed in an amount of from 1.0 to 5.0 mM, and having not more that 1.5 mM $NH_4^+$. A phosphorus compound at a concentration of at least 2.5 mM measured as phosphate is also included. A chelating agent such as EDTA, and an iron compound present in molar excess over the concentration of the chelating agent are employed to control divalent ion concentrations. Potassium ions are maintained at a concentration of below 14 mM. The use of media containing ammonium ions at less than 1.5 mM combined with a supply of reduced nitrogen in the form of arginine, with low potassium levels, has proved useful as media for organized growth, particularly for use with coniferous plants.

3 Claims, No Drawings

FORMULATIONS OF PLANT CULTURE MEDIA AND APPLICATIONS THEREFOR

This is a continuation of application Ser. No. 08/050,353, filed as PCT/AU91/00509, Nov. 4, 1991, published as WO92/07460, May 14, 1992, (now abandoned).

This invention relates to new formulations of culture media and applications of these for growth of plants and plant cells, tissues and organs.

This application has particular but not exclusive application to coniferous plants and to permitting growth and normal development of these plants in tissue culture, and for illustrative purposes reference will be made to such application. However, it is to be understood that this invention could be used in other applications, such as culture media suitable for other plant species.

It has been recognized that plant tissue culture methods may be useful to clonally multiply valuable plants through micropropagation and somatic embryogenesis procedures. Culture of plant cells may be useful in other ways, including generation of genetic diversity through somaclonal variants, regeneration of plants from protoplasts, cells, calli, and intra- or intergenic hybrid forms of these, regeneration of genetically modified plants from any such plant cells or structures, selection for resistance to any imposed or otherwise incurred stress, whether natural or artificial, the production of plants free from pathogens, the rejuvenation of mature tissues, the rescue of embryos from non-viable seeds, or the culture of plant cells, calli, or organs for production of plant secondary products or other valuable extracts.

In broad terms, tissue culture is conducted in a culture medium which is usually an aqueous nutrient composition. However, it has been found generally that few species and genotypes are adequately responsive to plant tissue-culture procedures for commercial application, and some species are recognized as particularly recalcitrant. The responses of many plant species are confined to specific genotypes. Coniferous plants are generally difficult, as are many other woody plants, and pine plants are particularly difficult. Where success is reported, this is limited to a fraction of the genotypes desired, with response frequencies within clonal populations (such as rooting frequency, regeneration frequencies generally) being relatively low with high attrition and/or slow growth characteristics.

It has been determined by the present applicant that a substantial reason for the failure of species and genotypes hitherto considered to be inherently recalcitrant to tissue culture lies in the selection of formulations of the nutrient media employed, it being determined that sub-optimal media and the resulting nutrient stresses imposed on the cultured plants are a primary cause of failure.

The present invention aims to alleviate deficiencies of the prior art culture media and to provide media which are reliable and efficient in use with the foregoing and other objects in view, this invention in one aspect resides broadly in an aqueous medium for plant tissue culture and including:

a nutritively effective concentration of reduced nitrogen, wherein said reduced nitrogen includes not more that 1.5 mM $NH_4^+$;

a phosphorus compound at a concentration of at least 2.5 mM measured as phosphate;

a chelating agent; and an iron compound present in molar excess over the concentration of said chelating agent.

Preferably, the source of reduced nitrogen includes an amino acid, with it being particularly preferred to use arginine as the predominant form of reduced nitrogen. Of course, combinations of amino acids and other forms of reduced nitrogen may be employed. The preferred arginine source of reduced nitrogen is advantageously employed in an amount of from 1.0 to 5.0 mM, with it being especially preferred to utilize an amount resulting in a concentration of about 2.5 mM.

The use of concentrations of ammonium ions of less than 1.5 mM in media for plant growth combined with a supply of reduced nitrogen in the form of arginine has not hitherto been reported as useful in the art of media formulation for organized growth, particularly for use with coniferous plants. Organised growth of embryos has been reported using media incorporating arginine or other organic forms of nitrogen, but in these media ammonium ions have been supplied at relatively high concentrations of at least 2.0 mM. It has become apparent that media in accordance with the present invention are advantageous since use of elevated ammonium ion concentrations tend to inhibit normal root development and detract from optimal shoot growth.

Preferably, the media in accordance with the present invention include a relatively low level of potassium ions, with it being preferred to utilize a concentration of potassium ions below 14 mM. It has been determined that there is an inhibitory effect of high levels of potassium ions on root development in tissue cultures such as are used in micropropagation of plants for transplantation.

Media in accordance with the present invention include a relatively high total phosphorus content of at least 2.5 mM measured as phosphate, it having been determined that high concentrations in media in accordance with the present invention provide for good root development in tissue culture specimens. Preferably, the phosphorus concentration measured as phosphate is from 2.5 mM to about 5.0 mM.

Preferably, the chelating agent is selected from Ethylene Diamine Tetra-acetic Acid (EDTA) and its derivatives. Where EDTA is selected as the chelating agent, an iron-to-chelate ratio of 1.2 or higher is preferred with it being particularly preferred to utilize an iron to chelate ratio of about 1.5. Of course the optimum ratio of iron to chelate will vary depending on the chelate selected and the concentrations of other transition metal ions present in the medium. In general, it has been determined that a guiding principle may be found in constructing media where the iron-chelate combination is non-stoichiometric in order to manipulate the complex equilibrium which regulates the availability of divalent metals in the medium.

Preferably, the total iron of the medium is between 120 µM and 180 µM, with the total EDTA of the medium preferably being in the range of 70 µM to 130 µM, with the requirement that the iron always be in stoichiometric excess over chelate in the medium.

Preferably, the stoichiometric excess of iron over chelate is at least 20 µM.

The media may include any of the additional nutrients and/or additives commonly utilized in growth media, including hormones, amino acids, vitamins, other minerals, pH buffers and the like. However, it is preferred that the sum of the total concentrations of the transition metals Zn, Cu, Ni and Co, not exceed the total level of chelate in the media.

Preferably, the media are selected from compositions in accordance with the following parameters.

|  | Range |
|---|---|
| Macroelements (mM) | |
| K | 5–14 |
| Mg | 0.5–1.5 |
| Ca | 2–4.5 |
| Na | 0.25–0.75 |
| $NH_4$ | 0.5–1.5 |
| $NO_3$ | 8–16 |
| $PO_4$ | 2.5–5 |
| $SO_4$ | 1.5–3.5 |
| Cl | 0.025–2.5 |
| Arginine | 2.0–3.5 |
| Microelements (μM) | |
| Fe | 120–180 |
| EDTA | 80–130 |
| Zn | 10–40 |
| Mn | 5–100 |
| Cu | 1–8 |
| Ni | 0–0.3 |
| Co | 0–0.3 |
| $H_3BO_3$ | 30–100 |
| $MoO_4$ | 0.05–0.2 |
| I | 0.5–6.0 |
| Vitamins and Carbohydrates (mg/l) | |
| Inositol | 50–1000 |
| Nicotinic Acid | 0.3–0.8 |
| Pyridoxine | 0.05–0.3 |
| Thiamine | 0.3–0.8 |
| Sucrose | 25000–55000 |

The invention will be further described with reference to the following Example.

EXAMPLE

|  |  |
|---|---|
| Macroelements (mM) | |
| K | 9 |
| Mg | 1 |
| Ca | 3 |
| Na | 0.5 |
| $NH_4$ | 1.0 |
| $NO_3$ | 11 |
| $PO_4$ | 4 |
| $SO_4$ | 2.5 |
| Cl | 0.1 |
| Arginine | 3.0 |
| Microelements (μM) | |
| Fe | 150 |
| EDTA | 100 |
| Zn | 20 |
| Mn | 10 |
| Cu | 5 |
| Ni | 0.1 |
| Co | 0.1 |
| $H_3BO_3$ | 60 |
| $MoO_4$ | 0.1 |
| I | 2.0 |
| Vitamins and Carbohydrates (mg/l) | |
| Inositol | 100 |
| Nicotinic Acid | 0.50 |
| Pyridoxine | 0.1 |
| Thiamine | 0.5 |
| Sucrose | 30000 |

A composition in accordance with the above embodiment is suitable for use as a general purpose culture medium for *P. radiata* culture processes, the medium proving efficacious for a wide range of genotypes. These processes include cell culture, callus culture, protoplast culture, shoot culture, root culture, meristem culture, micropropagation, embryo rescue, somatic embryogenesis, organogenesis, regeneration, transformation procedures, and any related methods.

The present medium was assessed through measurement of growth of *P. radiata* embryos in vitro compared with known benchmark media, namely, GD (Greshoff and Doy, 1972), LP Modified (von Arnold and Eriksson, 1981), and the LP Modified-like formulation MS (Murashige and Skoog, 1962). Embryo growth after 28 days of culture at 25° C. yielded the following comparative results:

| Formulation | Growth index (by wt.) |
|---|---|
| Present formulation | 1.0 |
| GD | 0.32 |
| LP Modified | 0.48 |
| MS | 0.48 |

Upon dissection of the embryos, it was determined as an average that the improvement in growth was primarily directed to root development, which accounted for about 75% of relative weight gain.

The described embodiment is a single medium formulation which provides the appropriate nutrient conditions for a wide range of responses. This medium will allow optimal or near optimal growth of both shoot and root apices, and will support growth of disorganised callus or cell cultures, to a moderate mass, at near-maximum rates. It is therefore particularly useful for use in supporting healthy developmental growth such as in shoot development, root development, and embryogenesis, provided appropriate hormones, as well as appropriate physical conditions and choice of tissue explant, are employed in conjunction with the nutrient medium. The composition is useful for avoiding stress-induced developmental aberrations, and stress-induced genetic variation.

The composition also has use as a base which can be modified in physiological and other studies of nutrient requirements where responses to specific nutrients can be obtained without incurring other growth-limiting nutrient conditions.

The medium is very suitable for most species of coniferous plants, but its use with any plant species is considered to be within the scope of the present invention.

It will of course be realised that while the above medium formulation has been given by way of example of this invention, all such and other modifications and variations thereto as would be apparent to persons skilled in the art are deemed to fall within the broad scope and ambit of this invention as defined in the claims appended hereto.

I claim:

1. A method of culturing coniferous plant tissue which comprises the step of propagating coniferous plant tissue in the presence of a medium comprised of reduced nitrogen comprising from 1.0 mM to 5.0 mM arginine and from 0.5 mM to 1.5 mM $NH_4^+$;

phosphate at a concentration of from 2.5 mM to 5.0 mM;

potassium ions at a concentration of from 5.0 mM to 14 mM;

a chelating agent present in an amount equivalent in chelating potential to EDTA in the range of 70 μM to 130 μM by addition; and an iron compound present at a concentration of between 120 μm and 180 μm and at least 20 μm over the concentration of the chelating agent.

2. A method according to claim 1 wherein said chelating agent is EDTA.

3. An aqueous medium for plant coniferous tissue culture and including:

|  | Range |
|---|---|
| Macroelements (mM) | |
| K | 5–14 |
| Mg | 0.5–1.5 |
| Ca | 2–4.5 |
| Na | 0.25–0.75 |
| $NH_4$ | 0.5–1.5 |
| $NO_3$ | 8–16 |
| $PO_4$ | 2.5–5 |
| $SO_4$ | 1.5–3.5 |
| Cl | 0.025–2.5 |
| Arginine | 2.0–3.5 |
| Microelements (µM) | |
| Fe | 120–180 |
| EDTA | 80–130 |
| Mn | 5–100 |

-continued

|  | Range |
|---|---|
| Cu | 1–8 |
| Ni | 0–0.3 |
| Co | 0–0.3 |
| $H_3BO_3$ | 30–100 |
| $MoO_4$ | 0.05–0.2 |
| I | 0.5–6.0 |
| Vitamins and Carbohydrates (mg/l) | |
| Inositol | 50–1000 |
| Nicotinic Acid | 0.3–0.8 |
| Pyridoxine | 0.05–0.3 |
| Thiamine | 0.3–0.8 |
| Sucrose | 25000–55000. |

\* \* \* \* \*